United States Patent
Wade et al.

[11] 3,946,010
[45] Mar. 23, 1976

[54] 3-PHENYL-2,5-DIHYDRO-AS-TRIAZIN-6(1H)-ONES

[75] Inventors: Peter C. Wade, Pennington, N.J.; B. Richard Vogt, Yardley, Pa.

[73] Assignee: E. R. Squibb & Sons, Inc., Princeton, N.J.

[22] Filed: Apr. 9, 1975

[21] Appl. No.: 566,552

[52] U.S. Cl............................ 260/248 AS; 424/249
[51] Int. Cl.². ........................................ C07D 253/06
[58] Field of Search............................ 260/248 AS

[56] References Cited
UNITED STATES PATENTS
3,883,525   5/1975   Mylari................................ 260/248

Primary Examiner—John M. Ford
Attorney, Agent, or Firm—Lawrence S. Levinson; Merle J. Smith; Burton Rodney

[57] ABSTRACT

Compounds of the structure

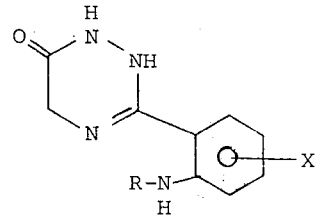

are provided which are useful as anti-inflammatory agents.

5 Claims, No Drawings

3-PHENYL-2,5-DIHYDRO-AS-TRIAZIN-6(1H)-ONES

Compounds having the structure

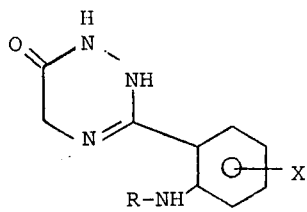

wherein R is lower alkyl, phenyl, or benzyl and X is hydrogen, halogen, nitro, trifluoromethyl, alkyl, alkoxy or alkylthio, are useful as anti-inflammatory agents.

The term "alkyl", as used throughout the specification, either by itself or as part of a larger group, refers to both straight and branched chain alkyl groups containing 1, 2, 3 or 4 carbon atoms.

The term "alkoxy", as used throughout the specification, refers to a group of the formula Y—O—, wherein Y is alkyl as defined above.

The term "halogen", as used throughout the specification, refers to fluorine, chlorine, bromine, and iodine.

Preferred are those compounds wherein R is alkyl and X is hydrogen or halogen; most preferred are those compounds wherein R is methyl and X is 5-Cl.

The compounds of formula I are useful in the treatment of inflammatory conditions in mammalian speices, e.g., rats, dogs, cats, monkeys, etc. and can be used to provide relief for joint tenderness and stiffness in conditions such as rheumatoid arthritis. Such compounds are formulated for use as anti-inflammatory agents according to accepted pharmaceutical practice in oral dosage forms such as tablets, capsules, elixirs or powders, or in an injectable form in a sterile aqueous vehicle prepared according to conventional pharmaceutical practice and may be administered in amounts of 100mg/70kg/day to 2g/70kg/day, preferably 100mg/70kg/day to 1g/70kg/day.

The novel compounds of this invention are prepared from compounds having the formula

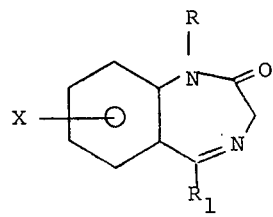

wherein X and R are as defined above and $R_1$ can be halogen (preferably bromine or chlorine), sulfhydryl, alkoxy, alkylthio, or phenyl-alkylthio. The compounds of formula II are known; see for example U.S. Pat. No. 3,414,563 and Swiss Pat. No. 485,742.

Reaction of a benzodiazepine of formula II with hydrazine yields a compound of formula I. The above reaction is preferably carried out in an inert atmosphere at room temperature, although elevated temperatures may be employed to improve yields and reduce reaction times.

It is to be understood that the compounds of formula I may be considered a tautomeric system of the two following possible forms:

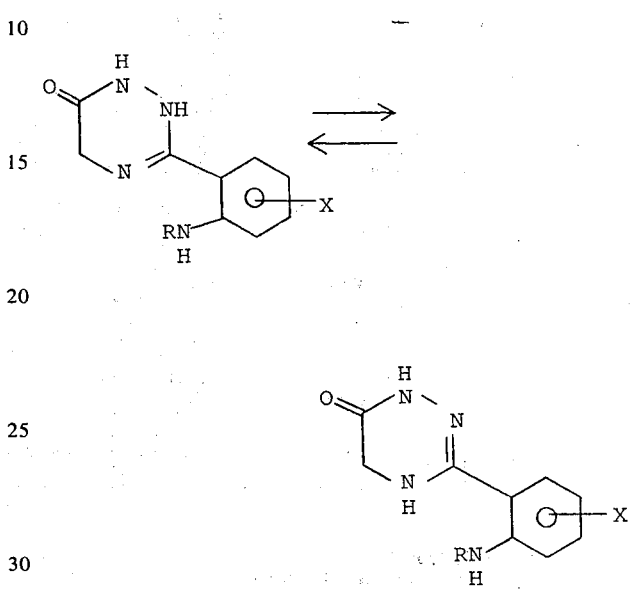

The compounds of formula I can be converted into pharmaceutically acceptable acid-addition salts using procedures well known in the art. Illustrative acid-addition salts are the hydrohalides, especially the hydrochloride and hydrobromide which are preferred, sulfate, nitrate, phosphate, tartrate, maleate, fumarate, citrate, succinate, methanesulfonate, benzenesulfonate, toluenesulfonate, and the like.

The following Examples represent preferred embodiments of the present invention. All temperatures are expressed in degrees Centigrade.

EXAMPLE 1

3-[5-Chloro-2-(methylamino)phenyl]-2,5-dihydro-as-triazin-6(1H)-one 5,7-Dichloro-1-methyl-1,4-benzodiazepinone-2 (6 g, 0.025 mol) is dissolved in 100 ml of anhydrous hydrazine and the mixture is stirred under an inert atmosphere at 25°. A precipitate forms after a few minutes and after two hours it is filtered off (2 g). The filtrate is allowed to stand for four days yielding another 2 g of crystals. The two crops (67% yield) are combined and recrystallized from methanol, and then chloroform, to give slightly yellow plates which are dried at 80° (5 mm) to yield the title compound, melting point 166°–167.5°.

EXAMPLES 2–11

Following the procedure of Example 1, but substituting the compound listed in column I for 5,7-dichloro-1-methyl-1,4-benzodiazepinone-2, the compound listed in column II is obtained.

| Example | Column I | Column II |
|---|---|---|
| 2. | 5-chloro-1-benzyl-7-(trifluoromethyl)-1,4-benzodiazepinone-2 | 3-[2-(benzylamino)-5-(trifluoromethyl)phenyl]-2,5-dihydro-as-triazin-6(1H)-one |
| 3. | 5-chloro-1-methyl-7-nitro-1,4-benzodiazepinone-2 | 3-[2-(methylamino)-5-nitrophenyl]-2,5-dihydro-as-triazin-6(1H)-one |
| 4. | 5-chloro-7-(ethylthio)-1-methyl-1,4-benzodiazepinone-2 | 3-[2-(methylamino)-5-(ethylthio)phenyl]-2,5-dihydro-as-triazin-6(1H)-one |
| 5. | 5-chloro-1,7-dimethyl-1,4-benzodiazepinone-2 | 3-[2-(methylamino)-5-methylphenyl]-2,5-dihydro-as-triazin-6(1H)-one |
| 6. | 5-chloro-1-methyl-7-(trifluoromethyl)-1,4-benzodiazepinone-2 | 3-[2-(methylamino)-5-(trifluoromethyl)phenyl]-2,5-dihydro-as-triazin-6(1H)-one |
| 7. | 8-bromo-5-ethoxy-1-phenyl-1,4-benzodiazepinone-2 | 3-[2-(phenylamino)-4-bromophenyl]-2,5-dihydro-as-triazin-6(1H)-one |
| 8. | 7-ethyl-1-benzyl-5-(methylthio)-1,4-benzodiazepinone-2 | 3-[2-(benzylamino)-5-ethylphenyl]-2,5-dihydro-as-triazin-6(1H)-one |
| 9. | 1-benzyl-1,4-benzodiazepin-2-one-5-thione | 3-[2-(benzylamino)phenyl]-2,5-dihydro-as-triazin-6(1H)-one |
| 10. | 5-chloro-1-phenyl-7-ethyl-1,4-benzodiazepinone-2 | 3-[2-(phenylamino)-5-ethylphenyl]-2,5-dihydro-as-triazin-6(1H)-one |
| 11. | 5-chloro-7-methoxy-1-methyl-1,4-benzodiazepinone-2 | 3-[2-(methylamino)-5-methoxyphenyl-2,5-dihydro-as-triazin-6(1H)-one |

What is claimed is:
1. A compound of the structure

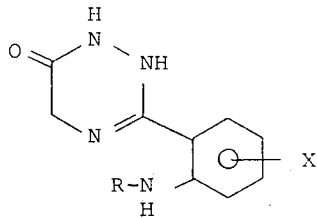

wherein R is selected from the group consisting of lower alkyl, phenyl and benzyl, and X is selected from the group consisting of hydrogen, halogen, nitro, cyano, trifluoromethyl, lower alkyl, lower alkoxy and lower alkylthio, tautomers thereof, and pharmaceutically acceptable acid-addition salts thereof.

2. The compounds as defined in claim 1 wherein R is alkyl.

3. The compound as defined in claim 1 wherein X is halogen, hydrogen or alkyl.

4. The compound as defined in claim 1 wherein R is alkyl and X is halogen.

5. The compound as defined in claim 4 having the name 3-[5-chloro-2-(methylamino)phenyl]-2,5-dihydro-as-triazin-6(1H)-one.

* * * * *

UNITED STATES PATENT AND TRADEMARK OFFICE
CERTIFICATE OF CORRECTION

PATENT NO. : 3,946,010
DATED : March 23, 1976
INVENTOR(S) : Peter C. Wade et al.

It is certified that error appears in the above-identified patent and that said Letters Patent are hereby corrected as shown below:

Column 1, line 5, insert the Roman numeral --I-- before the formula.

Signed and Sealed this eighteenth Day of May 1976

[SEAL]

Attest:

RUTH C. MASON
Attesting Officer

C. MARSHALL DANN
Commissioner of Patents and Trademarks